US00PP16052P2

(12) United States Plant Patent
Peerenboom

(10) Patent No.: US PP16,052 P2
(45) Date of Patent: Oct. 18, 2005

(54) ***BUXUS* PLANT NAMED 'PEERGOLD'**

(50) Latin Name: *Buxus microphylla*
Varietal Denomination: Peergold

(76) Inventor: Adrianus Antonius Peerenboom, Goordonksedÿk 10, Mariaheide 5464 TE (NL)

( * ) Notice: Subject to any disclaimer, the term of this patent is extended or adjusted under 35 U.S.C. 154(b) by 52 days.

(21) Appl. No.: 10/850,264

(22) Filed: May 21, 2004

(51) Int. Cl.[7] ..... A01H 5/00
(52) U.S. Cl. ..... Plt./226
(58) Field of Search ..... Plt./226

(56) References Cited

PUBLICATIONS

UPOV–ROM GTITM, Plant Variety Database, 2004/04, GTI Jouve Retrieval Software, Citation for Buxus 'Peergold'.*

* cited by examiner

*Primary Examiner*—Anne Marie Grunberg
*Assistant Examiner*—June Hwu

(57) ABSTRACT

A new cultivar of *Buxus microphylla* named 'Peergold' that is characterized by green and yellow-green variegated foliage which sets 'Peergold' apart from all other existing varieties of *Buxus* known to the inventor.

1 Drawing Sheet

Genus: *Buxus*. Species: *microphylla*.
Varietal denomination: 'Peergold'.

BACKGROUND OF THE INVENTION

The present invention relates to a new and distinct cultivar of small-leaved Boxwood (*Buxus*) grown as a low-growing ornamental evergreen shrub for use in the landscape and as an edging and low hedging plant in the garden. The new cultivar is known botanically as *Buxus microphylla* 'Peergold' and will be referred to hereinafter by the cultivar name 'Peergold'.

'Peergold' was discovered in 1994 as a branch sport on an individual plant of *Buxus microphylla* 'Faulkner' (unpatented) amongst a commercial crop of *Buxus microphylla* 'Faulkner' in production at the inventor's nursery in Mariaheide, The Netherlands.

The variety *Buxus microphylla* 'Faulkner' ordinarily grows with entirely green foliage. The individual branch discovered by the inventor exhibited yellow-green variegation as herein described. The inventor excised the variegated shoot in 1994, rooted it directly and allowed it to grow into a one year old plant. The plant, which was naturally self-branching, exhibited the same variegation as the initial branch sport. In 1995, the inventor removed from the one year old plant several shoots for use as cuttings for asexual propagation. Rooting was successful and the grown-on plants exhibited the characteristic variegation of the initial branch sport. All asexual propagations from the first rooting of the excised shoot cutting were conducted by the inventor or under the inventor's supervision and direction, and took place at the inventor's nursery in Mariaheide, The Netherlands. The inventor has determined that the distinguishing characteristic of variegation of the foliage has remained stable and uniform in successive generations.

When compared with the parent variety, *Buxus microphylla* 'Faulkner', 'Peergold' is distinguishable by pronounced yellow-green variegated foliage, whereas the foliage of the parent variety, *Buxus microphylla* 'Faulkner', is uniformly green. No other variegated forms of *Buxus microphylla* are known to inventor. Variegated forms of *Buxus sempervirens* exist in commerce, usually listed as *Buxus sempervirens variegata* whose foliage exhibits white or cream variegation.

An application for a grant of European Community Plant Breeders Rights for 'Peergold' was filed on Mar. 12, 2001, Serial Number 2001/0564. A grant of European Community Plant Breeders Rights was issued for 'Peergold' on Nov. 10, 2003, Grant Number 12037.

'Peergold' was first exhibited to the public at the Plantarium Nursery Show, Boskoop, The Netherlands on Aug. 20, 2003. The first distribution of any plants of 'Peergold' took place after this date.

SUMMARY OF THE INVENTION

The following represent the distinguishing characteristics of the new *Buxus microphylla* cultivar 'Peergold'. In combination these traits set 'Peergold' apart from all other existing varieties of *Buxus microphylla* known to the inventor. 'Peergold' has not been tested under all possible conditions and phenotypic differences may be observed with variations in environmental, climatic, and cultural conditions, however, without any variance in genotype.

1. 'Peergold' exhibits pronounced green and yellow-green variegated foliage.
2. 'Peergold' is slow-growing and achieves typically 24 cm–30 cm in height and 20 cm–30 cm in spread after four years of growth.
3. 'Peergold' has not been observed to flower.

BRIEF DESCRIPTION OF THE DRAWING

The accompanying color drawing illustrates the overall appearance of an entire plant of the new *Buxus microphylla* cultivar 'Peergold' showing the colors as true as it is reasonably possible to obtain in colored reproductions of this type.

Colors in the drawing may differ from the color values cited in the detailed botanical description, which accurately describe the actual colors of the new variety 'Peergold'. The illustrated plant is established in border soil at the inventor's nursery in Mariaheide, The Netherlands and is coming into its fourth year of growth from a cutting.

BOTANICAL DESCRIPTION OF THE PLANT

The following is a detailed description of the *Buxus microphylla* cultivar named 'Peergold'. Data was collected in June 2003 at Mariaheide, The Netherlands. The observed plant was in its fourth year of growth in open ground. Color determinations are in accordance with The Royal Horticultural Society Colour Chart, 2001 Edition, except where general color terms of ordinary dictionary significance are used. 'Peergold' has not been tested under all possible conditions and phenotypic differences may be observed with variations in environmental, climatic, and cultural conditions, however, without any variance in genotype. The growing requirements are similar to the species. Under normal growing conditions there are no known disease problems known to the inventor.

Botanical classification: *Buxus microphylla* 'Peergold'.
Use: Ornamental landscape plant.
Parent: 'Peergold' is a branch sport from the parent plant *Buxus microphylla* 'Faulkner' (unpatented).
Type: Evergreen shrub.
Vigor: Low.
Habit: Compact and low-growing: pinching unnecessary although will increase plant density.
Form: Flattened mound, with height approximately equal to spread.
Height: 24 cm–30 cm after four years from initial propagation.
Width: 20 cm–30 cm after four years.
Hardiness: USDA Zones 6–9.
Propagation: Softwood cuttings.
Root system: Fine and fibrous.
Soil: Plant in loam or clay soil.
Sunlight: Plant in full sunlight.
Time to initiate roots: 6–8 weeks are required at air temperature of 18–20° Centigrade for an initial cutting to produce roots.
Crop time: 18–24 months are required to produce a finished 1-liter container from a rooted cutting.
Diseases and pests: None known to inventor.
Stems:
- *Branching habit.*—Freely branching. No basal branching.
- *Number of branches.*—Approximately 150 branches including laterals.
- *Internode length.*—1.1 cm. between nodes, on average.
- *Stem diameter.*—2 mm. in diameter.
- *Stem length of an individual branch.*—15 cm.
- *Shape.*—Quadrangular.
- *Surface.*—Smooth, very slightly glossy.
- *Pubescence.*—Very short (less than 0.1 mm) greenish-white hairs at the young growth tips.
- *Stem color.*—144A and 144B both individually present.

Foliage:
- *Leaf arrangement.*—Opposite.
- *Leaf division.*—Simple.
- *Leaf number per lateral branch.*—Average 38 (19 pairs).
- *Leaf shape* (*young and mature*).—Ovate to broad elliptic; occasionally obovate.
- *Leaf base* (*young and mature*).—Acuminate.
- *Leaf apex* (*young and mature*).—Rounded.
- *Leaf venation.*—Pinnate.
- *Vein color for young and mature leaves (both surfaces).*—143B.
- *Pubescence.*—None present.
- *Margin.*—Entire.
- *Leaf surface* (*both surfaces*).—Smooth, leathery, glossy.
- *Leaf attachment.*—Petiolate.
- *Petiole length.*—1.5 mm.
- *Petiole shape and diameter.*—Flattened: diameter from 1.0 mm to 0.6 mm.
- *Petiole color.*—144A.
- *Petiole surface.*—Smooth.
- *Mature leaf dimensions.*—1.9 cm. in length and 1.1 cm. in width.
- *Young leaf dimensions.*—0.75 cm. in length and 0.5 cm. in width.
- *Mature leaf color* (*adaxial surface*).—Between 137A and 147A. Margins irregularly colored yellow-green N144A and N144B.
- *Mature leaf color* (*abaxial surface*).—143C. Margins irregularly colored yellow-green N144A and N144B.
- *Young leaf color* (*adaxial surface*).—Between 143A and 146B (more towards 146B). Margins irregularly colored yellow-green N144A and 144B.
- *Young leaf color* (*abaxial surface*).—144A. Margins irregularly colored yellow-green N144A.
- *Foliar fragrance.*—None observed.

Flower: Flowering has not been observed.
Reproductive organs: Not applicable.
Seed: Not applicable.

It is claimed:

1. A new and distinct variety of *Buxus microphylla* plant named 'Peergold' as described and illustrated.

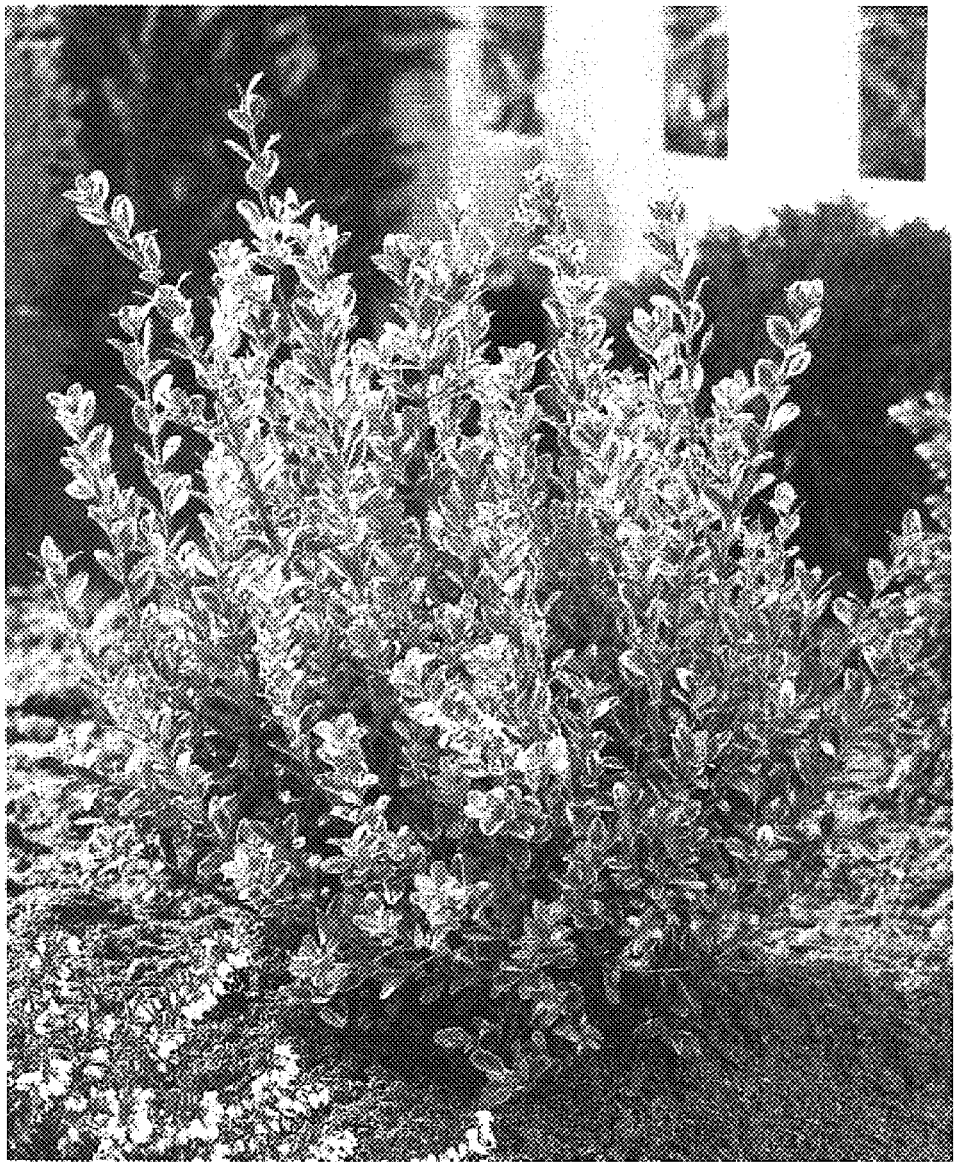

* * * * *